United States Patent [19]

Darden et al.

[11] 4,420,646

[45] Dec. 13, 1983

[54] FEEDSTOCKS FOR THE PRODUCTION OF SYNTHETIC LUBRICANTS

[75] Inventors: Jerome W. Darden; Lewis W. Watts, Jr.; Edward T. Marquis, all of Austin, Tex.

[73] Assignee: Texaco Inc., White Plains, N.Y.

[21] Appl. No.: 372,491

[22] Filed: Apr. 28, 1982

[51] Int. Cl.$^3$ .......................... C07C 1/16; C07C 3/18
[52] U.S. Cl. .......................... 585/10; 585/12; 585/18; 585/255; 585/510; 585/525; 585/643
[58] Field of Search ............ 585/10, 12, 18, 255, 585/510, 512, 520, 525, 526, 532, 643, 648, 660, 664

[56] References Cited

U.S. PATENT DOCUMENTS

| | | | |
|---|---|---|---|
| 3,152,998 | 10/1964 | Moss | 252/470 |
| 3,780,128 | 12/1973 | Shubkin | 585/255 |
| 4,042,488 | 8/1977 | Perciful | 585/648 |
| 4,045,508 | 8/1977 | Cupples et al. | 585/511 |
| 4,218,330 | 8/1980 | Shubkin | 585/255 |
| 4,300,006 | 11/1981 | Nelson | 585/255 |

*Primary Examiner*—Curtis R. Davis
*Attorney, Agent, or Firm*—Jack H. Park; Kenneth R. Priem; David L. Mossman

[57] ABSTRACT

Novel feedstocks for the production of synthetic lubricant base oils are described. The feedstock is a blend of internal and alpha olefins with the internal olefins comprising more than 50 but less than 99 weight percent of the blend. The alpha olefins may be derived from ethylene polymerization or wax pyrolysis. The olefins may be oligomerized over a boron trifluoride catalyst and a promoter. When the oligomers are hydrogenated they provide a synthetic lubricant base stock having excellent properties.

10 Claims, No Drawings

FEEDSTOCKS FOR THE PRODUCTION OF SYNTHETIC LUBRICANTS

CROSS-REFERENCE TO RELATED APPLICATIONS

This application is related to co-pending patent application Ser. No. 372,492, filed on Apr. 28, 1982, which is related to the manufacture of synthetic lubricant additives over boron trifluoride from olefin mixtures comprising 99 weight per cent or more of internal olefins.

This application is also related to co-pending patent application Ser. No. 372,367, filed on Apr. 27, 1982, which is concerned with a process for making synthetic lubricants via boron trifluoride from paraffins which have been dehydrogenated.

BACKGROUND OF THE INVENTION

1. Field of the Invention

The invention relates to methods of oligomerizing olefins over a boron trifluoride catalyst and more particularly relates to methods of oligomerizing a mixture of internal and alpha olefins.

2. Description of Related Methods

Many researchers have believed that the oligomers from internal olefins are unsuitable for use in synthetic lubricants. Nearly all patents issued on olefin oligomerization have involved alpha olefins only. For example, see U.S. Pat. No. 3,410,925 to Eby, et al. in which alpha olefins are mixed with alkylatable aromatic hydrocarbons over a Friedal-Crafts catalyst to form an alkylation sludge which is then mixed with olefins having 3 to 18 carbon atoms which are also passed over the catalyst to produce olefin dimers. U.S. Pat. No. 3,652,706 to Saines, et al. describes the polymerization of alpha olefins having 2 to 20 carbon atoms over a Friedel-Crafts metal halide catalyst plus a hydrogen form of mordenite to produce compounds having a molecular weight between 700 and 2,500. Production of a gasoline fuel composition is described in U.S. Pat. No. 3,749,560 to Perilstein which occurs by reacting a mixture of mono olefins over a Friedel-Crafts catalyst heated to a temperature around 145° C. to produce oligomers having molecular weights between 350 to 1,500. Also, U.S. Pat. No. 3,149,178 to Hamilton, et al. reveals an improved method for making polymerized olefin synthetic lubricants via a particular distillation technique of oligomers made from alpha mono olefins using a Friedel-Crafts catalyst. Alpha olefins having six to twelve carbon atoms may be dimerized in the presence of a Friedel-Crafts catalyst according to the method described in U.S. Pat. No. 4,172,855 to Shubkin, et al.

It is also known that the term "Friedel-Crafts catalysts" includes boron trifluoride among other metal halidetype Lewis catalysts, see *Kirk-Othmer Encyclopedia of Chemical Technology*, Third Edition, Vol. 11, Pg 292. Boron trifluoride has also been known to polymerize olefins, as seen in F. Albert Cotton, et al., *Advanced Inorganic Chemistry: A Comprehensive Text*, Interscience Publishers, 1962, p. 191.

A number of patents have also used $BF_3$ to oligomerize olefins. Close study will reveal that alpha olefins are considered the only useful form. For example, British Pat. No. 1,323,353 describes the use of wax cracked alpha olefins as precursors for synlube fluids. U.S. Pat. No. 2,780,664 to Serniuk describes the reaction of conjugated dienes with mono olefins over $BF_3$ promotoed by an ether mixed with a halo alkane diluent at a temperature from −30° to 100° C. to produce oligomers suitable for drying oils. Alpha olefins having from 5 to 20 carbon atoms are oligomerized using $BF_3$ plus an alcohol or water promoter as described in U.S. Pat. No. 3,382,291 to Brennan. In this patent, $BF_3$ and a mixture of $BF_3$ plus the promoter complex are introduced in two separate streams. Another U.S. patent by Brennan, U.S. Pat. No. 3,742,082, concerns the dimerization of alpha olefins via $BF_3$ which is promoted with phosphoric acid or water at a temperature from 100° to 150° C. U.S. Pat. No. 3,763,244 to Shubkin, which describes the oligomerization of n-alpha olefins having 6 to 16 carbon atoms over $BF_3$ promoted with water, at a temperature between 10° and 60° C. where it is preferred that $BF_3$ is added continuously.

Yet another U.S. patent to Brennan, U.S. Pat. No. 3,769,363 describes the oligomerization of olefins having 6 to 12 carbon atoms using $BF_3$ with a carboxylic acid promotor having at least 3 carbon atoms at a temperature between 0° and 20° C. to produce olefins heavy in trimer form. U.S. Pat. No. 3,780,128 also to Shubkin relates to the oligomerization of alpha olefins having 6 to 16 carbon atoms in which $BF_3$ is employed in a molar excess of alcohol. U.S. Pat. No. 3,876,720 to Heilman, et al. described a two-step procedure by which alpha olefins having 8 to 12 carbon atoms are converted to vinylidene olefins which are then reacted over a 1:1 molar complex of $BF_3$ and alcohol to produce oligomerized vinylindene olefins. A method for oligomerizing both short and long chain alpha olefins having from 14 to 20 carbon atoms simultaneously over $BF_3$ with an alcohol or water promoter at 0° to 60° C. with a monomer recycle is described in U.S. Pat. No. 4,225,739 to Nipe, et al. There is also U.S. Pat. No. 4,263,465 to Sheng, et al. which describes a two-step process for reacting one-butene with a higher alpha olefin over $BF_3$ in the presence of a proton donor at a temperature from −30° to 50° C. to produce an oligomer having 8 to 18 carbon atoms. The intermediate oligomer is reacted with other higher alpha mono olefins over the same catalyst system from −30° to 60° C. to produce oligomers having 20 to 40 carbon atoms. For more information on $BF_3$-catalyzed oligomerization of alpha olefins, see Brennan, "Wide-Temperature Range Synthetic Hydrocarbon Fluids," Ind. Eng. Chem. Prod. Res. Dev. 1980, Vol. 19, pp 2–6 and Shubkin, et al., "Olefin Oligomer Synethetic Lubricants: Structure and Mechanism of Formation," Ind. Eng. Chem. Prod. Res. Dev. 1980, Vol. 19, pp 15–19.

Two patents have been located which involve the reaction of internal olefins over Friedel-Crafts catalysts. U.S. Pat. No. 4,167,534 to Petrillo, et al. describes olefins which are both alpha and internal having from 10 to 15 carbon atoms which are reacted over Friedel-Crafts catalysts between 20° and 200° C. to produce oligomers. The catalysts used in the examples of this patent are only $AlCl_3$ and $NaAlCl_4$. The internal olefins are also those that are statistically distributed. U.S. Pat. No. 4,218,330 to Shubkin describes hydrogenated dimers from alpha olefins having from 12 to 18 carbon atoms, especially 1-tetradecene, made using a Friedel-Crafts catalyst, which includes therein boron trifluoride with a promoter. Shubkin's method uses predominantly alpha olefins, although the specification mentions that "fairly large amounts of internal olefins can be tolerated without adversely affecting the physical properties of the oligomer." This last remark from Shubkin reveals the general feeling of those working in the field that internal olefins do not produce oligomers with good properties for synthetic lubricants. For example, in U.S. Pat. No. 3,952,071 to Isa, et al., it is revealed that olefins may be oligomerized in the presence of a mixture of a polyhydric alcohol derivative and an aluminum halide. Isa, et al. mention that the olefin could be internal or alpha although alpha olefins are the only ones used in the examples therein. U.S. Pat. No. 3,947,509, also to Isa, et al., also claims that internal olefins may be used over a ketone and ester ether or alcohol promoted aluminum chloride catalyst although only alpha olefins are used in the examples.

U.S. Pat. No. 4,300,006 issued on Nov. 10, 1981. It describes a process for producing a hydrocarbon oil by contacting a mixture of alpha and at least 50 weight per cent internal olefins with a boron trifluoride dimerization catalyst. However, the productivity of useful products from the process revealed in U.S. Pat. No. 4,300,006 is quite low. For example, an alkane diluent is found to be necessary in the process described therein. When the lights and heavies are distilled out as required by the method, little useful product results. Further, this method requires a much longer reaction time and a higher catalyst concentration than desired. It would be beneficial if a method for producing synthetic lubricants could be devised which would overcome the aforementioned disadvantages.

In the field of oligomerizing olefins for synthetic lubricants, it is a continual problem to produce olefins having low viscosities at room temperature and below but which have a high viscosity index and low volatility.

SUMMARY OF THE INVENTION

The invention is concerned with a process for the oligomerization of mono olefins comprising contacting a mixture of alpha olefins and internal olefins comprising greater than 50 and less than 99 weight per cent of internal olefins where both the alpha and internal olefins each have between 9 and 24 carbon atoms inclusive, with a catalyst comprising boron trifluoride under oligomerization conditions.

DESCRIPTION OF THE PREFERRED EMBODIMENTS

It has been surprisingly discovered that oligomers which have an unusual blend of properties may be made by reacting alpha and internal mono olefins over a boron trifluoride catalyst and a promoter, where the internal olefin component is greater than 50 weight per cent and less than 99 weight per cent of the mixture. More preferably, the internal olefin component is greater than 50 and less than 90 weight per cent. No other researchers have accomplished this objective in this way.

The olefin feedstock may be generally expressed as a mixture of compounds comprising alpha olefins having the formula

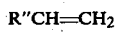
R″CH=CH$_2$ where R″ is an alkyl radical of 7 to 22 carbon atoms and internal olefins having the formula

RCH=CHR′ where R and R′ are the same or different alkyl radicals of 1 to 21 carbon atoms. However, the total number of carbon atoms in any one olefin molecule should be within the range of 9 to 24 inclusive, with an especially preferred range being between 13 and 15 inclusive.

The internal olefins used herein have the double bond randomly distributed across the molecule. In this context the term "randomly distributed" means that the double bond in the internal olefin is not predominantly in any one location. For example, an olefin mixture being comprised in the majority of alpha olefins would be outside the scope of this definition since the double bond would be located predominantly between the first and second carbon atoms of the molecules. Likewise, since the internal olefins used for oligomerization in the method of U.S. Pat. No. 4,300,006 are made by disproportionation of alpha olefins, the double bond is located predominantly at or near the center of the molecule and such olefin feedstocks also fall outside the definition of having a "random distribution" of the double bond. A random distribution includes the distribution one may obtain upon the dehydrogenation of paraffins. One would expect the double bond to be in all possible positions in the olefin molecules in a statistical or thermodynamic distribution.

The method of this invention employs some quantity of alpha olefin in the feedstock, preferably greater than 10 but less than 50 weight per cent. Co-pending patent application Ser. No. 372,492, filed on Apr. 28, 1982, relates to a method of oligomerization where the olefin feedstock consists essentially only of internal olefins. In reality, very small amounts of alpha olefins may be present in such a feedstock, but they are commonly present in quantities only of about 0.1 weight per cent and rarely as high as 1.0 weight per cent.

The alpha olefins to be oligomerized in this invention may be obtained by a multi-step process. In the first step, ethylene is transformed into linear alpha olefins using Ziegler technology as disclosed in various patents, including U.S. Pat. Nos. 3,424,815; 3,482,000; 3,424,816; 3,444,264; 3,444,263; 3,502,741; 3,510,539; 3,478,124; and 3,441,631. These patents are incorporated herein by reference. The result of this conversion of ethylene is a mixture of alpha olefins ranging from C-4 to above C-24. The alpha olefins ranging from about C-9 to C-24 or any other range of alpha olefins desired within C-9 to C-24 are separated and oligomerized using boron trifluoride and a protonic promoter. The alpha olefins of below about 9 and above about 24 carbon atoms are combined and subjected to an isomerization/disproportionation process described in the literature, for example: U.S. Pat. Nos. 3,647,906; 3,728,414 and 3,726,938,, which are incorporated herein by reference.

The olefins resulting from this isomerization/disproportionation process are a mixture of alpha and internal olefins of various molecular weights. The olefins should have a total number of carbon atoms in the range from about 9 to 24 or any selected cut within that range may be oligomerized with boron trifluoride and a protonic promoter. Optionally, those olefins may be mixed with the alpha olefins from the initial ethylene made feed and oligomerized.

Such a process provides a systematic way to control which olefin cut is selected for oligomerization, and also uses the discarded cuts for additional feed. Olefins useful in the method of this invention may also be produced by wax pyrolysis.

Generally, both kinds of olefins should have between 9 and 24 carbon atoms, inclusive. It is especially preferred that the olefins have between 13 and 15 carbon atoms inclusive. Internal olefin mixtures are potentially more available than the pure cut alpha olefins and are potentially as cheap or cheaper than the corresponding pure cut alphas. It will be shown that the method of this invention affords higher quality products than those obtained with prior art catalysts $AlCl_3$ and $NaAlCl_4$ and those obtained with $BF_3$ using alpha olefins only as the feed.

The catalyst of choice is boron trifluoride. A number of different kinds of promoters may be used, such as alcohols, carboxylic acids or water. It is especially preferred that 1-butanol be used as the promoter. The temperature range at which the oligomerization may be performed successfully is between 25° and 150° C., with a preferred range between 65° to 105° C. As shown later, it is especially preferred that the reaction temperature be about 75° to 85° C. The pressure range of the reaction may run from zero to 1,000 psig. The oligomerization of the olefins may be conducted in a batch or continuous mode.

In order to form materials which have adequate oxidative stability for lubricants, the oligomerized olefins are optionally hydrogenated either partially or totally. This hydrogenation is done by procedures known to those skilled in the art as exemplified by U.S. Pat. Nos. 4,045,508; 4,013,736; 3,997,622 and 3,997,621. A particularly preferred catalyst for this hydrogenation is a nickel-copper-chromia catalyst described in U.S. Pat. No. 3,152,998, incorporated by reference herein. A cobalt-copper-chromium catalyst would also be useful.

While the methods of others in the field include a distillation step after the hydrogenation procedure to obtain products of various 210° F. viscosities, it is much preferred in the method of the invention that no further distillation (beyond monomer flashing) be conducted. In other words, the monomer-stripped, hydrogenated bottoms are the desired synthetic lubricant components. Thus the method of this invention does not require the costly, customary distillation step, yet surprisingly produced a synthetic lubricant component that has excellent properties and that performs in a superior fashion. However, it is also anticipated that one skilled in the art may find subsequent distillation useful in the practice of this invention.

The monomer stripping step should be conducted under mild conditions. It was discovered that distillations conducted at high temperature, 210°–290° C., would cause the oligomers to break down in some fashion and come off as volatiles. It is, therefore, important that monomer removal be accomplished at as mild conditions as possible; that is, the reboiler or pot temperature should preferably be kept at or under 180° C. when stripping out monomer.

First, the experimental methods will be described, and then the results will be tabulated.

COMPARATIVE EXAMPLES

A number of comparative oligomerization examples were run using the procedures of U.S. Pat. No. 4,167,534, the disclosure of which is incorporated by reference herein. It is believed that this patent constitutes one of the closest prior art. The examples herein were patterned after Examples 1, 5 and 7 therein. These examples were chosen because they represented a wide variety of conditions, particularly temperature. The primary variable in the comparative examples is the olefin feed material, although sometimes twice the amount of $AlCl_3$ used in the U.S. Pat. No. 4,167,534 patent is employed in an attempt to improve the conversion. The internal olefins used in all of these examples is a $C_{13-14}$ blend comprising 56 weight per cent of $C_{13}$ internal olefin and produced by Shell's Higher Olefin Process (SHOP) of Shell Chemical Co.

According to the disclosure in U.S. Pat. No. 4,167,534, Example 1 is begun by heating the feedstock to 80° C. The feedstock is then added over 15 minutes with 1% $AlCl_3$. The temperature is then raised to 100° C. and maintained for 100 minutes. The product is then discharged, separated from the heavy catalytic layer, washed with caustic solution and then distilled.

Example 5 begins by adding the olefin feed at room temperature with 1% $AlCl_3$ in only one portion. The temperature is allowed to rise on its own for 120 minutes. The product is then discharged, separated from the heavy catalytic layer, washed with caustic solution and distilled.

The feed in Example 7 of U.S. Pat. No. 4,167,534 is added at 130° C. with 5% $NaAlCl_4$ over 90 minutes. The reaction mass is then maintained at 130° C. for 60 minutes further. The product is then discharged, separated from the heavy catalytic layer, washed with caustic solution and distilled. The results of the comparative examples are shown in Table I.

TABLE I

COMPARATIVE EXAMPLES

| | | | | | | Properties of Hydrogenated Stripped Oligomer | | | | |
|---|---|---|---|---|---|---|---|---|---|---|
| | Reaction Conditions | | Temperature, | Method of U.S. Pat. No. 4,167,534 | Conversion Basis | % Bottoms Basis Olefin | Viscosity, centistokes, | | | Pour Point, | TGA: % Sample Remaining |
| Example | Feed | Catalyst | °C. | Used | LC | Charged | 210° F. | 25° C. | VI | °C. | at 233° C. |
| 1 | $C_{13-14}$ int. | $AlCl_3$ | 80 | Ex. 1 | 32.5 | 21.6 | 5.69 | 56.00 | 127.4 | −50 | 91.8 |
| 2 | $C_{13-14}$ int. | $AlCl_3$* | 80 | Ex. 1 | 42.2 | 29.2 | 5.85 | 60.96 | 121.4 | <−50 | 91.3 |
| 3 | $C_{11-14}$ int. | $AlCl_3$ | 80 | Ex. 1 | | 21.0 | 6.79 | 80.39 | 116.9 | <−50 | 88.5 |
| 4 | $C_{14}$ alpha | $AlCl_3$ | 80 | Ex. 1 | 85.9 | 80.2 | 22.07 | 341.83 | 129.9 | +20 | 98.2 |
| 5 | $C_{13-14}$ int. | $AlCl_3$ | R.T.** | Ex. 5 | 24.8 | 16.8 | 6.40 | 68.90 | 124.4 | −50 | 92.2 |
| 6 | $C_{13-14}$ int. | $AlCl_3$* | R.T. | Ex. 5 | 45.6 | 27.4 | 6.43 | 71.75 | 122.1 | <−50 | 91.4 |
| 7 | $C_{11-14}$ int. | $AlCl_3$ | R.T. | Ex. 5 | 36.8 | 23.2 | 7.12 | 86.72 | 116.5 | <−50 | 89.5 |
| 8 | $C_{14}$ alpha | $AlCl_3$ | R.T. | Ex. 5 | 93.9 | 87.6 | 18.20 | 260.91 | 131.2 | +10 | 98.3 |
| 9 | $C_{13-14}$ int. | $NaAlCl_4$ | 130 | Ex. 7 | 42.0 | 30.3 | 5.20 | 48.68 | 125.9 | <−50 | 88.2 |
| 10 | $C_{11-14}$ int. | $NaAlCl_4$ | 130 | Ex. 7 | 68.9 | 44.8 | 6.96 | 87.04 | 114.0 | −45 | 91.3 |

TABLE I-continued
COMPARATIVE EXAMPLES

| | Reaction Conditions | | Temperature, °C. | Method of U.S. Pat. No. 4,167,534 Used | Conversion Basis LC | % Bottoms Basis Olefin Charged | Properties of Hydrogenated Stripped Oligomer | | | | |
|---|---|---|---|---|---|---|---|---|---|---|---|
| | | | | | | | Viscosity, centistokes. | | | Pour Point, °C. | TGA: % Sample Remaining at 233° C. |
| Example | Feed | Catalyst | | | | | 210° F. | 25° C. | VI | | |
| 11 | $C_{14}$ alpha | $NaAlCl_4$ | 130 | Ex. 7 | 100.0 | 87.1 | 19.44 | 286.80 | 130.5 | +15 | 96.0 |

*Twice as much $AlCl_3$ was used in these examples as described in the examples of U.S. Pat. No. 4,167,534
**R.T. means room temperature With respect to the results outlined in Table I, the conversion is a weight per cent of monomer oligomerized as determined by liquid chromatography. The weight per cent of the bottoms as based on the olefin charged is given in the next column. While these two columns of data generally measure the same concept (notice the qualitative correlation), the applicants prefer to use "% conversion" while the inventors in U.S. Pat. No. 4,167,534 used the "% bottoms" method. Both are employed in the examples of Table I for comparative purposes.

Viscosities at two standard temperatures are given in centistokes. The viscosity index (VI) is the change in viscosity with temperature such that the higher the number, the lower is the change in viscosity with temperature. Conversely, a low VI signifies a large change in viscosity with temperature. Pour point is a measure of the temperature, in degrees Centigrade, at which the sample will begin to pour. Below that temperature the composition may generally be regarded as a solid. Thermogravimetric analysis (TGA) is a test which measures volatility by measuring the weight per cent of sample remaining at various temperatures as the temperature is raised in a slow, uniform manner. When a sample's TGA indicates that at least 80% remains at 233° C., the sample is considered sufficiently non-volatile to be useful in lube oil formulations. A good oligomer mixture has less than a 10% distillation loss at about 700° F.

EXAMPLES ILLUSTRATING THE INVENTION

The following examples illustrate the method of the invention using $BF_3$ as the catalyst and an internal/alpha mixture as the olefin feed. Two examples are included using $C_{14}$ alpha olefin as the feedstock to show that an inferior oligomer mixture is produced.

EXAMPLE 12

To a 1 gallon stainless steel autoclave were charged 500 g of feed. The feed consisted of a mixture of 945 g $C_{14}$ alpha olefin made by Gulf Oil Chemicals Co., and 1145 g $C_{13}$-$C_{14}$ internal olefin. Thirty-two grams of $BF_3$ were then added with stirring. The clave was heated to 35°-40° C. To the mixture were added 1600 g of the feed along with 19 g 1-butanol slowly over a 3 hour period. The mixture was stirred at 35°-40° C. for 1.5 hours, then hydrolyzed with water. After three water washes of 200 ml each, a sample was dried and submitted for liquid chromatography analysis. Liquid chromatography showed 4% monomer, 37% dimer, 41% trimer, 15% tetramer, and 3% pentamer.

EXAMPLE 13

Oligomerization

To a 1 liter round bottom flask fitted with magnetic stirrer, thermometer, $BF_3$ sparge tube, and dropping funnel was added 220 g $C_{13}$-$C_{14}$ internal olefin made by Shell Chemical Co. The solution was heated to 75° C. under nitrogen purge. The solution was saturated with $BF_3$. To the dropping funnel was added 200 g $C_{14}$ alpha olefin from Shell Chemical Co. made from ethylene polymerization, and 3.9 g 1-butanol. The contents of the dropping funnel were added over a 10 minute period, and the solution heated to 85° C. The mixture's temperature was held at 85° C. for 1 hour, cooled to room temperature, and water washed three times to hydrolyze $BF_3$. Liquid chromatography analysis showed 7% monomer, 59% dimer, 26% trimer, and 8% tetramer.

Hydrogenation

To a stainless steel autoclave was charged 353 g of the oligomer obtained in the above step followed by 17.7 g of finely ground nickel-copper-chromia catalyst. This catalyst is described in U.S. Pat. No. 3,152,998, incorporated by reference herein. The clave was pressured to 1,000 psig with hydrogen and heated to 210° C. The clave was repressured to 2,000 psig where the contents were held at 210° C. with stirring for four hours. Hydrogenation methods and catalysts are well known to those skilled in the art, and it is ancitipated that any of these methods could be used in conjunction with the method of this invention. As is well known, such hydrogenations may be performed in either batch or continuous modes.

Monomer Removal

To a 500 ml round bottom flask equipped with magnetic stirrer and thermometer were added 310.8 g of the hydrogenated, nickel free oligomer from the above step. The pot was heated to 190°-195° C. at 0.20 mm Hg, and subsequently 87.6% of the charge was recovered as bottoms product. Liquid chromatography analysis of the bottoms product showed 57% dimer, 27% trimer, 12 % tetramer and 4% pentamer.

Oligomer Properties

The oligomer obtained in this example had the following properties: 210° F. viscosity of 4.27 centistokes, viscosity index of 132, 92.2% remaining in TGA at 233° C., −30° C. viscosity of 1070 centipoise, and pour point of −35° F.

EXAMPLE 14

Oligomerization

To a 2 liter round bottom flask fitted as in Example 13 was added 404 g $C_{13}$-$C_{14}$ internal olefin from Shell Chemical Co. that was 56% $C_{13}$. The solution was heated to 75° C. under nitrogen purge, then saturated with $BF_3$. The dropping funnel was filled with 54 g $C_{14}$ alpha olefin from Shell Chemical Co. and 46 g of $C_{13}$-$C_{14}$ internal olefin (56% $C_{13}$) and 4.5 g 1-butanol. Contents of the dropping funnel were added over 10 minutes, then heated to 85° C. and held for one hour. The BF$_3$ was neutralized with Na$_2$CO$_3$ and the solution water washed two times. Liquid chromatography analysis showed 11% monomer, 65% dimer, 20% trimer, and 4% tetramer.

Hydrogenation

To a stainless steel autoclave was added 441.7 g of the product obtained in the above step followed by 22.1 g of nickel-copper-chromia catalyst. The clave was pressured to 1,000 psig with hydrogen and heated to 210° C. The clave was repressured to 2,000 psig, heated and stirred at 210° C. for 4 hours.

Monomer Removal

To a 1,000 ml flask fitted with thermometer and magnetic stirrer was added 398.5 g of the nickel free hydrogenated product from the above step. The blend was heated to a pot temperature of 200° C. at 0.35 mm Hg. Subsequently, 81.8% of the charge was recovered as bottoms. Liquid chromatography analysis of the product showed 67% dimer, 25% trimer, and 8% tetramer and pentamer.

Oligomer Properties

The oligomer of this example had the following properties: 210° F. viscosity of 3.92 cs, viscosity index of 125.9, pour point of less than −50° F., and 90.7% remaining in TGA at 233° C.

EXAMPLE 15

To a 1 liter flask fitted with magnetic stirrer, thermometer, BF$_3$ sparge tube, condenser, and dropping funnel were added 225 g C$_{13}$-C$_{14}$ internal olefins from Shell Chemical Co. These internal olefins are 56 weight percent C$_{13}$ and are the same ones used in Examples 16 and 17. The solution was purged with nitrogen for 30 minutes, then saturated with BF$_3$. The dropping funnel was filled with 220 g C$_{13}$-C$_{15}$ wax cracked alpha olefins from Chevron Chemical Co. having the following composition: 40% C$_{13}$, 40% C$_{14}$, and 20% C$_{15}$. These alpha olefins were also the ones used in Examples 16 and 17. Also added to the dropping funnel were 4 g of 1-butanol. Two hundred grams of the contents of the dropping funnel were added over a two hour period at 35°-40° C. Boron trifluoride was present in excess. After another hour, water was added to hydrolyze BF$_3$. The solution was washed three times. Liquid chromatography analysis of the product showed 75% monomer, 18% dimer, and 7% trimer.

EXAMPLE 16

Oligomerization

To a 1 liter flask fitted as in Example 15 were added 225 g of C$_{13}$-C$_{14}$ internal olefin and 0.6 g 1-butanol. The apparatus was purged with nitrogen for 30 minutes, then saturated with BF$_3$. The dropping funnel was filled with 110 g of C$_{13}$-C$_{14}$ internal olefin, 110 g C$_{13}$-C$_{15}$ wax cracked alpha olefins, and 3.3 g of 1-butanol. Two hundred grams of this feed were added over a two hour period at 25° C. The blend was heated to 85° and held there for 0.5 hours. The solution was cooled to room temperature and the BF$_3$ hydrolyzed with water. Liquid chromatography analysis of the product showed 7% monomer, 56% dimer, 25% trimer, and 12% tetramer and pentamer.

Monomer Removal

To a 1 liter pot fitted with magnetic stirrer and thermometer was added 373.8 g of the product from the above step. The monomer was removed by heating to a pot temperature of 190° with pressure at 1.2 mm Hg. Subsequently, 87.3% of the charge weight was recovered as bottoms. Liquid chromatography analysis showed a trace of monomer, 58% dimer, 28% trimer, and 13% tetramer and pentamer.

Hydrogenation

To a stainless steel autoclave were charged 286.5 g of the monomer free product from the above step, along with 14.3 g of nickel-copper-chromia hydrogenation catalyst. The clave was pressured to 1,000 psig with hydrogen, and the contents heated to 210° C. The clave was repressured to 2,000 psig, and the contents stirred and reacted for four hours at 210° C.

Oligomer Properties

The monomer free, hydrogenated product of this example had the following properties: 210° F. viscosity of 4.16 centistokes, pour point of −50° F., a viscosity index of 135.9, and 87.3% remaining at 233° C. in TGA.

EXAMPLE 17

Oligomerization

To a 500 ml flask fitted as in Example 15 were added 200 g C$_{13}$-C$_{14}$ internal olefin and 45 g C$_{13}$-C$_{15}$ wax cracked alpha olefins. The mixture was heated to 75° under nitrogen purge, then saturated with BF$_3$. The dropping funnel was filled with 50 g C$_{13}$-C$_{14}$ internal olefin and 15 g C$_{13}$-C$_{15}$ wax cracked alpha olefin and 2.8 g of 1-butanol. The contents of the dropping funnel were added to the pot over a one hour period. The blend was heated to 85° and allowed to react for an additional hour. Boron trifluoride was neutralized with Na$_2$CO$_3$ in water, and the blend washed with water twice. Liquid chromatography analysis showed 20% monomer, 56% dimer, 16% trimer, and 8% tetramer.

Hydrogenation

To a stainless steel autoclave were charged 265.0 g of the product obtained in the above step and 13.3 g of nickel-copper-chromia hydrogenation catalyst. The clave was pressured to 1,000 psig with hydrogen and heated to 210° C. The clave was repressured to 2,000 psig, and the contents stirred and heated at 210° C. for four hours.

Monomer Removal

To a 500 ml flask were charged 222.1 g of the nickel free, hydrogenated product from the above step. The pot was equipped with magnetic stirrer and thermometer. The contents of the pot were heated to 190°-195° C. pot temperature with 0.10-0.20 mm Hg. Subsequently, 65.6% of the charge was recovered as bottoms. Liquid chromatography analysis showed 73% dimer, 20% trimer, and 7% tetramer.

Oligomer Properties

The bottoms product from the step above had the following properties: 210° F. viscosity of 3.91 centistokes, viscosity index of 131.4, pour point of −50° F., 90.7% remaining in TGA at 233° C.

EXAMPLE 18

This example was run for additional comparison. Only $C_{14}$ alpha olefins were used as the feedstock.

To a 300 ml stainless steel clave (316 SS) was charged 158.6 g of olefin and 0.7 of 1-butanol. The clave was sealed and heated to approximately 98° C. at which time $BF_3$ gas was introduced in amounts ranging from 2.2 to 2.8 g (average 2.5 g $BF_3$ per run). The reaction was stirred and allowed to exotherm on its own (no cooling). The reaction was stirred for 60 minutes (time measured from first $BF_3$ addition and $BF_3$ added over a 3–6 minute period) and then cooling water turned on. The cool reaction mixture was neutralized with 10 grams of $Na_2CO_3$ and 100 ml water. After layer separation, the organic layer was washed twice more with fresh water and dried. The oligomer was analyzed (GPC/LC) for conversion and subjected to hydrogenation at 210° C. for two hours at 2,000 psig hydrogen pressure in the presence of a nickel-copper-chromium oxide catalyst (5% by weight basis weight oligomer).

EXAMPLE 19

This example is another comparative example using only $C_{14}$ alpha olefins as the feedstock. The procedure is identical to the procedure in Example 18 except that the temperature of the reaction mixture (olefin and promoter) before $BF_3$ addition was 65° C. (instead of 98° C.) and the amount of $BF_3$ added ranged from 2.2 g to 4.0 g (3.0 g average). Conversions and properties of the oligomers from Examples 12 through 19 are summarized in Table II.

stokes at 25° C., a viscosity between 3.5 and 5.0 centistokes at 210° F., a viscosity index of greater than 100 and a thermogravimetric analysis value of greater than 80 weight percent.

Also from Table II, Examples 12–17, it may be seen that a better oligomer distribution is obtained (higher dimer component) if the reaction temperature is about 75° to 85° C. This range is the especially preferred oligomerization temperature.

It should be noted that the amount of catalyst used in the method of this invention (about 1.4 to 2.8 weight percent of the olefin feed) is notably less than the amount of catalyst used in other methods in the field, such as the method disclosed in U.S. Pat. No. 4,300,006 (2.6 to 6.1 wt. %). In further contrast with the method of this particular patent, no employment of a diluent, no heavies or lights (except monomers) removal and a shorter reaction time are features of the inventive method.

In addition, it should be noted that the method revealed in U.S. Pat. No. 4,300,006, incorporated by reference herein, requires that the dimerization feedstock be obtained from the disproportionation of alpha olefins having 8 to 10 carbon atoms. As a result, the dimerization feedstocks therein are a mixture of alpha and internal olefins where the alpha olefins have slightly more than half the carbon number of the corresponding internal olefin and the internal olefins are highly symmetrical (being formed from the disproportionation of two alpha olefins). The inventive method uses instead alpha and internal olefins having identical or close carbon numbers, and internal olefins where the double bond is

TABLE II

EXAMPLES ILLUSTRATING THE INVENTION

| | Feed, wt. %, | | Temp., | Weight Percent* | | | | Properties of Hydrogenated Stripped Oligomer | | | |
|---|---|---|---|---|---|---|---|---|---|---|---|
| Example | Alpha | Internal | °C. | Monomer | Dimer | Trimer | Higher | Viscosity, centistokes, 210° F. | VI | Pour Point, °C. | TGA: % Sample Remaining at 233° C. |
| 12 | 45.2 $C_{14}$ | 54.8 $C_{13-14}$ | 35–40 | 4 | 37 | 41 | 18 | — | — | — | — |
| 13 | 47.6 $C_{14}$ | 52.3 $C_{13-14}$ | 75–85 | 7 | 59 | 26 | 8 | 4.27 | 132 | −37 | 92.2 |
| 14 | 10.7 $C_{14}$ | 89.3 $C_{13-14}$ | 75–85 | 11 | 65 | 20 | 4 | 3.92 | 125.9 | <−45 | 90.7 |
| 15 | 47.1 $C_{13-15}$ | 52.9 $C_{13-14}$ | 35–40 | 75 | 18 | 7 | — | — | — | — | — |
| 16 | 23.5 $C_{13-15}$ | 76.5 $C_{13-14}$ | 85 | 7 | 56 | 25 | 12 | 4.16 | 135.9 | −45 | 87.3 |
| 17 | 19.4 $C_{13-15}$ | 80.6 $C_{13-14}$ | 75–85 | 20 | 56 | 16 | 8 | 3.91 | 131.4 | −45 | 90.7 |
| 18 | 100 $C_{14}$ | — | 98 | — | — | — | — | 4.27 | 134.3 | −35 | 98.8 |
| 19 | 100 $C_{14}$ | — | 65 | — | — | — | — | 4.41 | 148.6 | −30 | 93.5 |

*Before monomer removal step

By comparing Tables I and II, it may be noted that the oligomers of this invention (Examples 12–17) are superior to the oligomers made from alpha olefin feedstocks only or those made with internal olefin feedstocks but a different catalyst (Examples 1–11 and 18–19). The 210° F. viscosities for the oligomers made from the inventive method are the same as or lower than those of any of the comparative examples. What is surprising is that the viscosity index values and TGA results for the oligomers of this invention are in the same range as those of the comparative examples. It was also unexpected to find that the pour points for Examples 13, 14, 16 and 17 were lower than for the most comparable Examples 18 and 19. It is especially surprising to find that oligomers made from predominantly internal olefins, long thought to be unsuitable, have a combination of favorable properties including improved viscosities and pour points. No particular property seems to have suffered from the use of internal olefins.

Preferably, a "4 centistoke fluid" (measured at 210° F.) should have a viscosity between 25 and 40 centirandomly distributed instead of located near the center of a symmetrical mono olefin. These differences in the feedstocks cause important differences in the properties of the resulting oligomers, as shown by the following examples involving $C_{14}$ internal olefin and $C_8$ alpha olefin as a mixed feedstock.

EXAMPLE 20

Oligomerization

The oligomerization of a 70 wt. % $C_{14}$ internal olefin and 30 wt. % $C_8$ alpha olefin mixture was accomplished over 2.5 g of a boron trifluoride catalyst with 1.1 g of 1-butanol as a protonic promoter and initiated at 95.1° C.

To a dry and clean 300 ml Hastelloy C autoclave were added 119 g of $C_{14}$ internal olefin from Shell Chemical Company's Higher Olefin Process (SHOP). The double bond in these internal olefins is randomly distributed throughout the molecule. Added at the same time were 51 g of $C_8$ alpha (1-octene from Aldrich Chemical Company, Inc.). At the time this was the closest approximation possible of the U.S. Pat. No. 4,300,006 feedstock. These additions were followed by 1.1 g of 1-butanol promoter. The clave was sealed and the contents heated to 91.5° C. with stirring. Starting at 95.1° C., $BF_3$ gas was introduced by adding four shots of $BF_3$ over an 11 minute period (2.5 g total $BF_3$ added) to the stirred reaction mixture. At the end of 17 minutes (measured from the first $BF_3$ addition), the temperature had risen 110.2° C. for a maximum exotherm of 15.1° C. One hour after the first $BF_3$ addition the reaction temperature was 101.5° C. The heat was turned off and cooling water turned on. The reaction mixture was neutralized with an aqueous $Na_2CO_3$ solution and water washed twice more. The organic layer was separated and dried by filtering through folded filter paper to obtain a net weight of 156.3 g. Liquid chromatography analysis indicated 31.9% of the material was $C_8$, $C_{14}$ or $C_{16}$ and 27.5% was dimer $C_{22}$ (from $C_8$ and $C_{14}$) and 32.2% was dimer $C_{28}$ (from $C_{14}$ and $C_{14}$) while 8.3% was $C_{36}$ or heavier. Conversion to material higher than $C_6$ was about 68.1%. The ratio of dimer to trimer and heavies was 7.19:1.

Hydrogenation and Stripping

A 1-liter stirred 316 stainless steel clave was charged with 144.5 g of oligomer from the previous step and 7.2 g of a nickel-copper-chromium oxide hydrogenation catalyst. The clave was flushed with hydrogen three or four times and pressured to 1,000 psig with hydrogen. Subsequently the clave was heated to 210° C. (the pressure increased to only 1,200 psig) and pressurized again to 2,000 psig with hydrogen. The reaction mixture was stirred at 210° C. for four hours during which the pressure remained at 2,000 psig. The hydrogenated oligomer was filtered and 137.3 g subjected to high vacuum stripping. The material was distilled through a jacketed column (with about 12 inches of Goodloe packing) until the head temperature reached 105° C. at 0.06 mm Hg. The bottoms weighed 67.1 g (49.6% of the total material, overhead plus bottoms) and the overhead weighed 68.1 g (50.4% of the total material). The bottoms product had a 210° F. viscosity of 3.6 cs, a 25° C. viscosity of 27.4 cs, a pour point of $<-50°$ F. and a viscosity index of 110. Liquid chromatography analysis indicated the presence of 25.5% dimer ($C_{22}$), 60.2% dimer ($C_{28}$) and 14.3% heavier materials. The TGA of the bottoms product indicated volatility was moderately high (85.0% sample remained at 233° C. in TGA of 10° C./minute).

EXAMPLE 21

Oligomerization

Oligomerization of a 70% $C_{14}$ internal olefin-30% $C_8$ alpha olefin mixture catalyzed by 2.2 g of $BF_3$ with 1.1 g of 1-butanol as a promoter was initiated at 94.9° C. As in the previous example, 119 g of $C_{14}$ internal olefin were added to a 300 ml clave along with 51 g of $C_8$ alpha olefin followed by 1.1 g of 1-butanol. The clave was sealed and heated to 94.9° C. Starting at 94.9° C., $BF_3$ gas was added over an 11 minute period (totalling 2.2 g of $BF_3$) to produce a 15.1° C. maximum exotherm after 16 minutes had elapsed after the first $BF_3$ addition. After a one hour reaction time measured from the first $BF_3$ addition, the mixture was cooled and neutralized with aqueous sodium carbonate. The organic layer was separated and dried by filtering through folded filter paper, to give a net weight of 162.5 g. Liquid chromatography analysis indicated 31.1% of the material was $C_8$, $C_{14}$ or $C_{16}$ and 27.2% was dimer $C_{22}$ and 33.4% was dimer $C_{28}$ while 8.3% was $C_{36}$ or heavier. Conversion to materials higher than $C_{16}$ was 68.9%. The ratio of dimer to trimer and heavies was 7.30:1.

Hydrogenation and Stripping

From the above step, 145.0 g of the oligomer was hydrogenated over 7.2 g of nickel-copper-chromium oxide catalyst. The hydrogenation was conducted at 210° C. and 2,000 psig from hydrogen for four hours. It was followed by filtration and stripping as described in the previous example. The bottoms products amounting to 55.3% of the change had a 25° C. viscosity of 25.7 cs and a 210° F. viscosity of 3.45 cs. The pour point of the bottoms material was $-40°$ F. and the viscosity index was 109.0. Liquid chromatography analysis indicated 33.6% dimer $C_{22}$ and 53.8% dimer $C_{28}$ and 12.6% heavies. The ratio of dimer to trimer and heavier was thus 6.94:1. The TGA indicated that the material was definitely too volatile; 82.1% sample remaining.

EXAMPLE 22

Oligomerization

Oligomerization of a 70% $C_{14}$ internal olefin-30% $C_8$ alpha olefin mixture catalyzed by 2.5 g $BF_3$ and 1.1 g 1-butanol as promoter was conducted starting at 75.1° C. To a clean and dry 300 ml clave was added 119 g of $C_{14}$ internal olefin and 51 g of $C_8$ alpha olefin of the same sources as the previous two examples, followed by 1.1 g of 1-butanol promoter. The clave was sealed and heated to 75.1° C. and at that temperature $BF_3$ gas was added in increments (shots) over a 10 minute period. Five separate shots were applied to total 2.5 g. Eleven minutes after the first $BF_3$ addition, the reaction temperature had risen to 100.7° C. (a maximum exotherm of 25.6° C.). The reaction was held at 75° C. for 1.5 hours total and then cooled and worked up as in the previous examples. The dry product from this lower temperature oligomerization had the following liquid chromatography analysis: 12.7% of monomer ($C_8$, $C_{14}$ and $C_{16}$), 23.7% of $C_{22}$, 42.1% of $C_{28}$ and 21.4% of trimer and heavies. Conversion to materials greater than $C_{16}$ was 87.3% with the dimer to trimer and heavies being 3.07:1.

Hydrogenation and Stripping

Hydrogenation of the oligomer from the above step was completed at 210° C., 4.0 hours and 2,000 psig hydrogen pressure. Workup (filtration) followed by high vacuum stripping afforded a bottoms product which amounted to 70.7% of the charge and had the following properties: 210° F. viscosity of 4.16 cs, 25° C. viscosity of 34.5 cs, pour point of $<-50°$ F. and a viscosity index of 124.2. The liquid chromatography analysis indicated 16.7% of the material was $C_{22}$, 56.8% was $C_{28}$ and 26.5% was heavies. TGA indicated the sample had excellent volatility (90% remaining at 233° C.).

EXAMPLES 23-31

Examples 23-28 were conducted in a manner similar to Examples 20-21 except that certain parameters were changed as shown in Table III.

Examples 29-31 were conducted according to the following procedure. Eighty-three grams of delta 7 $C_{14}$ and 36 g of delta 9 $C_{18}$ internal olefin and 51 g of $C_8$ alpha olefin were added to a 300 ml Hastelloy clave followed by 1.1 g of 1-butanol. This olefin mixture is the closest approximation to the U.S. Pat. No. 4,300,006 feedstocks obtainable with the materials on hand. The clave was sealed and $BF_3$ introduced in the indicated quantities. Work-up was conducted as usual involving an aqueous $Na_2CO_3$ wash followed by two water washes and filtering the organic layer through filter paper to dry it. Hydrogenation was accomplished at 210° C. and in the presence of 5% (by weight, basis olefin) nickel catalyst and 2,000 psig hydrogen pressure for four hours. The hydrogenation product was filtered and distilled at high vacuum (<0.1 mm Hg) and to a head temperature of 110° C. The bottoms product was submitted for analysis. The results of this last set of comparative examples are summarized in Table III.

25-28 utilizing the feeds of this invention with the U.S. Pat. No. 4,300,006 conditions indicate similar and in some cases worse results; the products had higher 210° F. viscosities and higher pour points than desired.

One way of expressing the fact that the alpha and internal olefins have carbon numbers in proximity (the feedstocks useful in this invention) is to say that the carbon numbers of the alpha and internal olefins are identical to or within one carbon of each other. For example, if an alpha olefin had a carbon number of 14 then the internal olefin present should have a carbon number in the range from 13 to 15, inclusive. Of course, if the olefin mixture had two alpha olefins of 13 and 14 carbons then internal olefins could have 12 to 15 carbon atoms, inclusive. As defined, the carbon numbers of the alpha olefins can likewise range around the carbon numbers of the internal olefins. It should be noted that the definition does not require that olefins of the permissible carbon numbers be present, only that the carbon num-

TABLE III

EXPERIMENTS USING LOWER MOLECULAR WEIGHT ALPHA AND HIGHER MOLECULAR WEIGHT INTERNAL OLEFINS AS FEEDSTOCKS

| | Feedstock, wt. %, | | Reaction Temp., °C. | Reaction Time, Hours | $BF_3$ Added, Grams | Maximum Exotherm, °C. | Liquid Chromatography | | % Bottoms | Properties of Hydrogenated Stripped Oligomers | | | | |
|---|---|---|---|---|---|---|---|---|---|---|---|---|---|---|
| | | | | | | | | Dimer, Trimer and Heavies | | Centistokes, | | VI | Pour Point, °F. | TGA |
| Ex. | Internal | Alpha | | | | | Conv. | | | 210° F. | 25° C. | | | |
| 20 | 70 $C_{14}$ | 30 $C_8$ | 95.1-110.2 | 1.0 | 2.5 | 15.1 | 68.1 | 7.19:1 | 49.6 | 3.80 | 27.4 | 110.0 | <−50 | 85.0 |
| 21 | 70 $C_{14}$ | 30 $C_8$ | 94.9-110.0 | 1.0 | 2.2 | 15.1 | 68.9 | 7.30:1 | 55.3 | 3.45 | 25.7 | 109.0 | −40 | 82.1 |
| 22 | 70 $C_{14}$ | 30 $C_8$ | 75.1-100.7 | 1.5 | 2.5 | 25.6 | 87.3 | 3.07:1 | 70.7 | 4.16 | 34.5 | 124.2 | <−50 | 90.0 |
| 23 | 70 $C_{14}$ | 30 $C_8$ | 75.0-96.4 | 1.5 | 2.5 | 21.9 | 93.5 | 1.55:1 | — | — | — | — | — | 86.0 |
| 24 | 48.8 Δ7 $C_{14}$ + 21.2 Δ9 $C_{18}$ | 30 $C_8$ | 75.1-97.4 | 1.5 | 2.1 | 22.3 | 83.1 | — | 83.5 | 3.41 | 24.3 | 108.9 | +20 | 76.4 |
| 25 | 70 $C_{14}$ | 30 $C_8$ | 25.0-47.8 | 1.5 | 2.6 | 22.8 | 82.0 | 3.74:1 | 81.9 | 4.91 | 40.8 | 138.6 | −15 | 92.9 |
| 26 | 70 $C_{14}$ | 30 $C_8$ | 25.0-28.1 | 6.5 | 2.4 | 3.1* | 21.4 | 6.38:1 | 15.5 | — | — | — | — | 83.8 |
| 27 | 70 $C_{14}$ | 30 $C_8$ | 25.0-54.5 | 1.5 | 5.4 | 29.4 | 96.9 | 0.93:1 | 93.5 | 4.99 | 45.0 | 125.6 | −35 | 92.0 |
| 28 | 70 $C_{14}$ | 30 $C_8$ | 25.0-55.8 | 6.5 | 5.4 | 30.7 | 97.3 | 0.65:1 | 92.8 | 5.91 | 58.4 | 126.9 | −45 | 93.6 |
| 29 | 48.8 Δ7 $C_{14}$ + 21.1 Δ9 $C_{18}$ | 30 $C_8$ | 25.2-44.4 | 1.5 | 2.5 | 19.2 | 86.1 | — | 72.0 | 4.40 | 37.1 | 120.3 | <−50 | 90.3 |
| 30 | 48.8 Δ7 $C_{14}$ + 21.1 Δ9 $C_{18}$ | 30 $C_8$ | 25.1-41.7 | 1.5 | 5.1 | 21.6 | 93.1 | — | 85.0 | 4.67 | 39.2 | 123.6 | <−50 | 90.0 |
| 31 | 48.8 Δ7 $C_{14}$ + 21.1 Δ9 $C_{18}$ | 30 $C_8$ | 25.1-51.1 | 6.5 | 5.5 | 26.0 | 96.4 | — | 85.2 | 5.63 | 54.0 | 123.2 | −40 | 94.0 |

*This reaction never started.

As can be seen from Table III, the product from the feedstocks used in U.S. Pat. No. 4,300,006 are unsuitable for use as a synthetic lubricant without further distillation; i.e., the bottoms product found useful using the method of the invention are superior. Examples 29-31 have 210° F. and 25° C. viscosities which are too high for use as 4 cs synthetic lubricants. One skilled in the art would not expect these materials to pass cold cranking tests. These same feedstocks when run at a higher temperatures produce a material with a low viscosity index and a poor TGA value (see Example 24).

Thus it is determined by comparative examples using the conditions of U.S. Pat. No. 4,300,006 that the resulting products would need to be distilled in order to meet the 4.0 cs 210° F. viscosity requirement and apparently the cold-cranking specifications as well. Examples bers of the alpha and internal olefins be in proximity. If a mixture included an alpha olefin of 8 and an internal olefin of 14 carbon atoms (such as a disproportionation product), it would fall outside the proximity definition.

Emphasis should be placed on the fact that the synthetic lubricant components of the instant invention are preferably used without further distillation, after the monomer removal and hydrogenation steps. In other words, the undistilled bottoms are the finished synthetic lubricant component. Typically, other oligomer mixtures must be distilled into "2 centistoke", "4 centistoke", "6 centistock", etc. fractions before they can be useful. The viscosities refer to the viscosity of the component at 210° F. Components made by the method of this invention make perfectly good "4 centistoke" components without distillation. Thus, the method of this invention does not require a costly distillation step, which is an important advantage over methods used by others in the field.

Many modifications may be made in the method of this invention without departing from its scope which is defined only by the appended claims. For example, it would be expected that one skilled in the art could change the $BF_3$ promoter, the temperature, the pressure or the modes of addition in trying to maximize the conversion or the oligomer properties.

We claim:

1. A process for oligomerizing mono olefins comprising contacting a mixture of alpha olefins and internal olefins comprising greater than 50 and less than 99 weight percent of internal olefins where both the alpha and internal olefins each have between 9 and 24 carbon atoms, inclusive, and the alpha and internal olefins have carbon numbers identical to or within one carbon number of each other and in which the internal olefins have the double bond randomly distributed, with a catalyst comprising boron trifluoride and a protonic promoter under oligomerization conditions to produce a crude oligomer product, removing only the unreacted monomer and hydrogenating the remainder.

2. A synthetic lubricant component prepared according to the process of claim 1.

3. A synthetic lubricant component having a viscosity at 210° F. of between 3.5 and 5.0 centistokes, a viscosity at 25° C. of between 25 and 40 centistokes, a viscosity index of greater than 100 and a thermogravimetric analysis value of greater than 80 weight percent, being produced by oligomerizing a mixture of alpha olefins and internal olefins having greater than 50 but less than 99 weight percent of internal olefins and both alpha and internal olefins each having between 9 and 24 carbon atoms, inclusive, and the alpha and internal olefins have carbon numbers identical to or within one carbon number of each other and in which the internal olefins have the double bond randomly distributed, by means of reacting the mixture of olefins in the presence of boron trifluoride catalyst and a protonic promoter at a temperature between 25° and 150° C. to produce a crude oligomer product, removing only the unreacted monomer and hydrogenating the remainder.

4. A process for the production of a synthetic lubricant component comprising oligomerizing a mixture of alpha and internal olefins having between 13 and 15 carbon atoms inclusive, in which the alpha and internal olefins have carbon numbers identical to or within one carbon of each other and in which the internal olefins have the double bond randomly distributed, the mixture being comprised of greater than 50 but less than 90 weight percent internal olefins, by reacting the mixture of olefins in the presence of a boron trifluoride catalyst and a protonic promoter at a temperature between 25° and 150° C. separating out only the monomer and hydrogenating the remainder to produce a synthetic lubricant component having a viscosity at 210° F. of between 3.5 and 5.0 centistokes, a viscosity at 25° C. of between 25.0 and 40.0 centistokes, a viscosity index of greater than 100 and a thermogravimetric analysis value of greater than 80 weight percent.

5. A synthetic lubricant component comprising a hydrogenated mixture of oligomers obtained by oligomerizing a mixture of alpha and internal olefins having between 9 and 24 carbon atoms inclusive, in which the alpha and internal olefins have carbon numbers identical to or within one carbon number of each other and in which the internal olefins have the double bond randomly distributed, and having greater than 50 but less than 99 weight percent of the olefin mixture as internal olefin, separating off any unreacted monomer as the only separation step and hydrogenating the remainder to produce a hydrogenated mixture of oligomers having a 210° F. viscosity between about 3.5 and 5.0 centistokes, a 25° C. viscosity between about 25 and 40 centistokes, a viscosity index of greater than 100 and a thermogravimetric analysis value of greater than 80 weight percent remaining at 233° C., the oligomers being composed of 2 or more but less than 10 oligomer units.

6. The synthetic lubricant component of claim 5 in which the mixture of alpha and internal olefins is comprised of greater than 50 but less than 90 weight percent internal olefins and both kinds of olefins have between 13 and 15 carbon atoms inclusive.

7. A process for the production of a synthetic lubricant component comprising
   (a) oligomerizing a mixture of alpha and internal olefins having between 9 and 24 carbon atoms inclusive, in which the alpha and internal olefins have carbon numbers identical to or within one carbon number of each other and in which the internal olefins have the double bond randomly distributed, the mixture being comprised of greater than 50 but less than 99 weight percent internal olefins, by reacting the mixture of olefins in the presence of a boron trifluoride catalyst and a protonic promoter at a temperature sufficient to produce a crude oligomer product,
   (b) neutralizing the crude oligomer product,
   (c) removing the organic layer from the neutralized crude product,
   (d) hydrogenating the oligomer product, and
   (e) stripping the unreacted monomer from the organic layer of the crude oligomer product as the only separation step.

8. The process of claim 7 in which the oligomerization step (a) is conducted at a temperature between 25° and 150° C.

9. The process of claim 7 in which both the alpha and internal olefins of the olefin mixture have between 13 and 15 carbon atoms, inclusive, and the mixture is comprised of greater than 50 but less than 90 weight percent of internal olefins and the resulting synthetic lubricant component having a viscosity at 210° F. of between 3.5 and 5.0 centistokes, a viscosity at 25° C. of between 25.0 and 40.0 centistokes, a viscosity index of greater than 100 and a thermogravimetric analysis value of greater than 80 weight percent.

10. A synthetic lubricant component prepared according to the process of claim 7.

* * * * *